US011439194B2

(12) United States Patent
Istook et al.

(10) Patent No.: US 11,439,194 B2
(45) Date of Patent: Sep. 13, 2022

(54) DEVICES AND METHODS FOR EXTRACTING BODY MEASUREMENTS FROM 2D IMAGES

(71) Applicant: North Carolina State University, Raleigh, NC (US)

(72) Inventors: Cynthia L. Istook, Raleigh, NC (US); Andre J. West, Raleigh, NC (US); Sibei Xia, Raleigh, NC (US); Jiayin Li, Raleigh, NC (US); James Beebe Hawes Collier, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 407 days.

(21) Appl. No.: 16/636,992

(22) PCT Filed: Aug. 10, 2018

(86) PCT No.: PCT/US2018/046248
§ 371 (c)(1),
(2) Date: Feb. 6, 2020

(87) PCT Pub. No.: WO2019/032982
PCT Pub. Date: Feb. 14, 2019

(65) Prior Publication Data
US 2020/0367590 A1 Nov. 26, 2020

Related U.S. Application Data

(60) Provisional application No. 62/544,165, filed on Aug. 11, 2017.

(51) Int. Cl.
*A41H 1/02* (2006.01)
*A41H 1/06* (2006.01)
(Continued)

(52) U.S. Cl.
CPC ............... *A41H 1/02* (2013.01); *A41H 1/06* (2013.01); *G06V 10/754* (2022.01);
(Continued)

(58) Field of Classification Search
None
See application file for complete search history.

(56) References Cited

U.S. PATENT DOCUMENTS

2002/0138170 A1* 9/2002 Onyshkevych ........ G06Q 30/06
700/130
2002/0166254 A1 11/2002 Liebermann
(Continued)

FOREIGN PATENT DOCUMENTS

WO 2004008898 A1 1/2004

OTHER PUBLICATIONS

International Search Report for International Application No. PCT/US2018/046248, dated Oct. 24, 2018.
(Continued)

*Primary Examiner* — Frank S Chen
(74) *Attorney, Agent, or Firm* — Thomas|Horstemeyer, LLP

(57) ABSTRACT

Various examples are provided for obtaining body measurements of a user, predicting body measurements of a user, and/or the like. Examples include a coded dimensioning garment having a stretchable fabric that conforms to a wearer's body without substantial compression or distortion of the skin. The garment can include measurement markings of known sizes at one or more known locations on the fabric. Methods are provided for predicting body measurements from a user. Image(s) of a user wearing the garment in a reference pose are captured and can be uploaded to a body measurement application. The real-world dimensions can be converted to pixel dimensions in the same ratio as the real (Continued)

world dimensions and inputted into a prediction model to generate measurements from areas of interest on the user.

13 Claims, 16 Drawing Sheets

(51) Int. Cl.
  *G06V 10/75* (2022.01)
  *G06V 40/10* (2022.01)
  *G06T 7/50* (2017.01)
(52) U.S. Cl.
  CPC .............. *G06V 40/103* (2022.01); *G06T 7/50* (2017.01); *G06T 2207/30196* (2013.01); *G06T 2210/16* (2013.01)

(56) References Cited

U.S. PATENT DOCUMENTS

| | | |
|---|---|---|
| 2005/0022708 A1 | 2/2005 | Lee |
| 2006/0140463 A1 | 6/2006 | Rutschmann |
| 2007/0133850 A1* | 6/2007 | Paez .................... G06T 7/60 382/128 |
| 2010/0064408 A1* | 3/2010 | Kemper ............ A41D 13/1209 2/243.1 |
| 2010/0319100 A1 | 12/2010 | Chen et al. |
| 2012/0095589 A1 | 4/2012 | Vapnik |
| 2013/0179288 A1 | 7/2013 | Moses et al. |
| 2016/0165988 A1* | 6/2016 | Glasgow ............ G06Q 30/0269 703/11 |
| 2017/0079339 A1* | 3/2017 | Yeomans ................ A41D 13/02 |
| 2018/0103694 A1* | 4/2018 | Fortenbacher ..... A41D 13/0051 |
| 2019/0272679 A1* | 9/2019 | Brodsky ................ G06F 30/20 |

OTHER PUBLICATIONS

Written Opinion for International Application No. PCT/US2018/046248, dated Oct. 24, 2018.

* cited by examiner

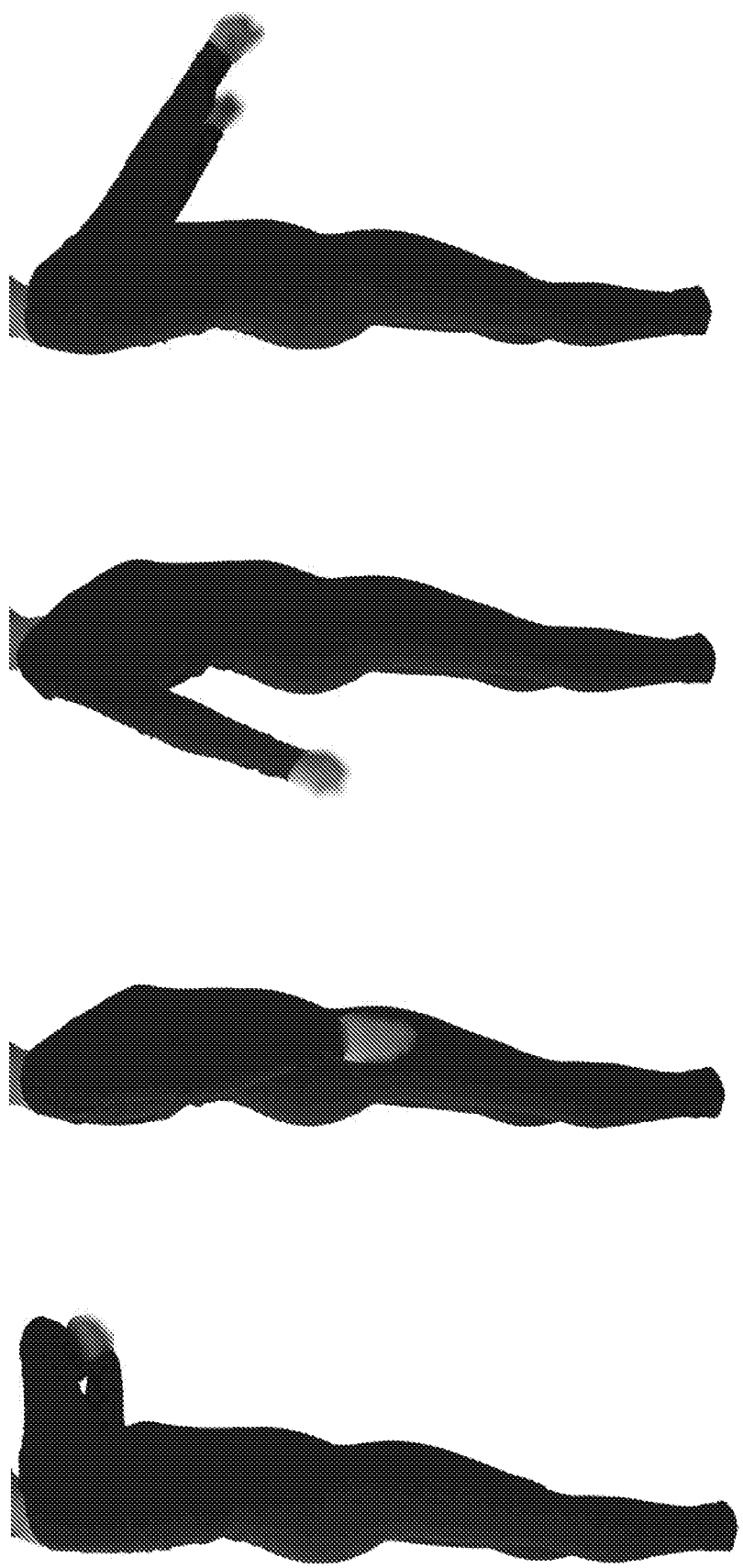

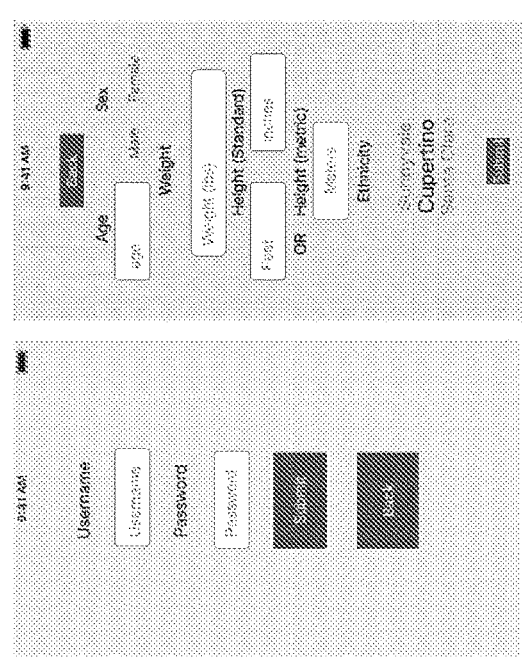
Fig. 10A  Fig. 10B  Fig. 10C  Fig. 10D
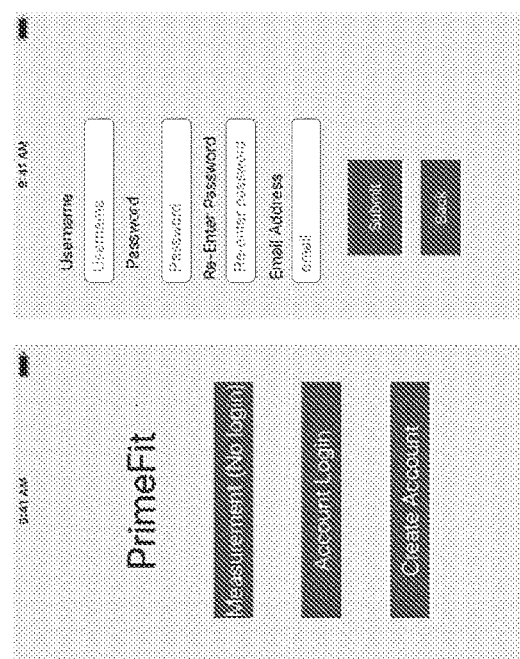
Fig. 10E  Fig. 10F  Fig. 10G  Fig. 10H
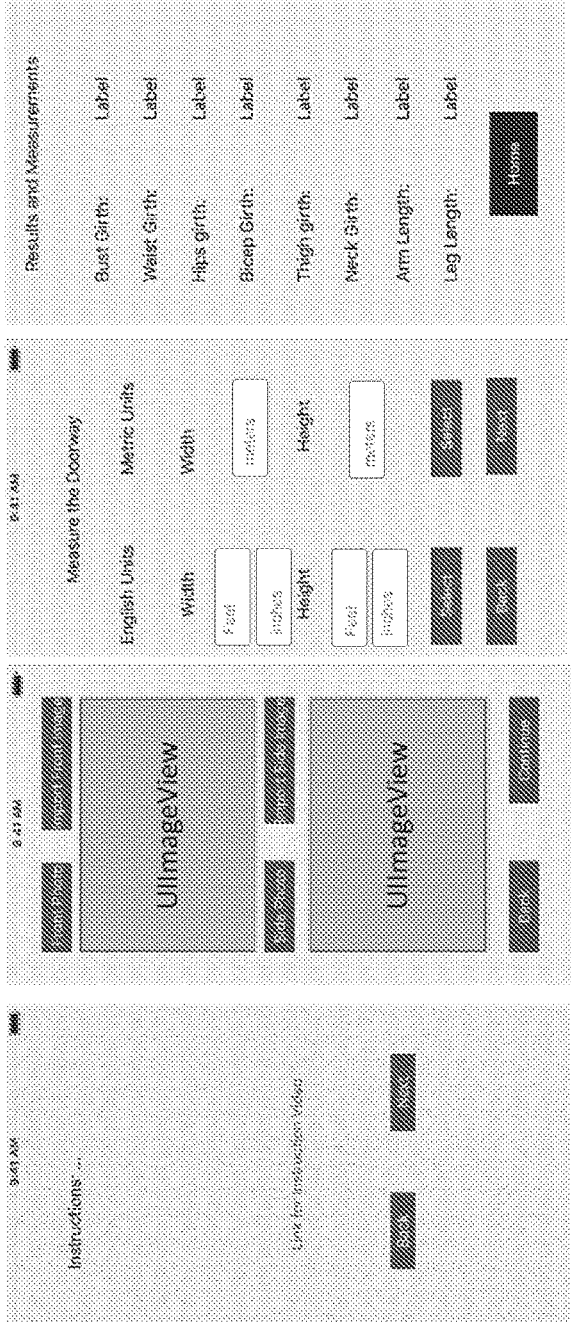

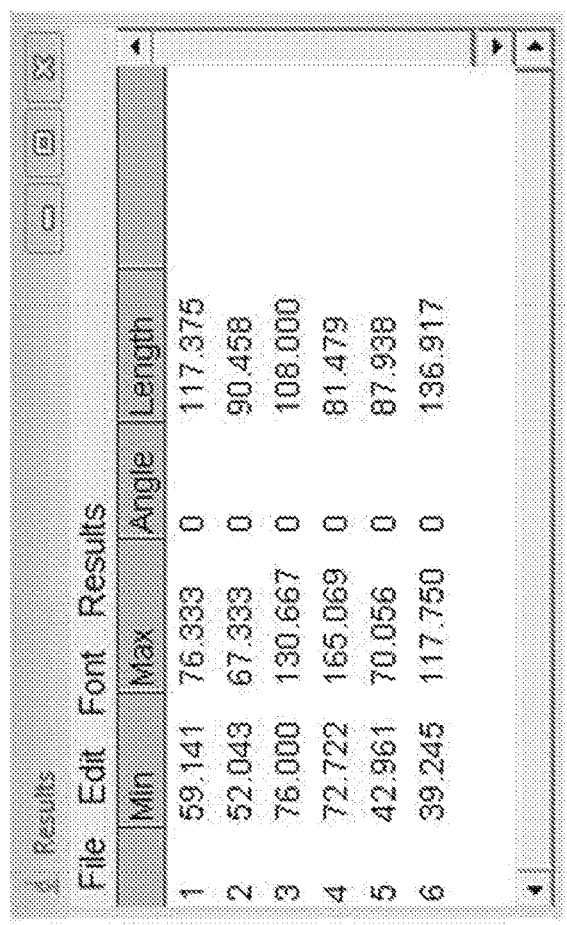
Fig. 14C
Fig. 14B
Fig. 14A

DEVICES AND METHODS FOR EXTRACTING BODY MEASUREMENTS FROM 2D IMAGES

CROSS-REFERENCE TO RELATED APPLICATIONS

This application is the 35 U.S.C. § 371 national stage of PCT application having serial number PCT/US2018/046248, filed on Aug. 10, 2018. This application also claims the benefit of and priority to U.S. Provisional Application Ser. No. 62/544,165, having the title "DEVICES AND METHODS FOR EXTRACTING BODY MEASUREMENTS FROM 2D IMAGES", filed on Aug. 11, 2018, the disclosure of which is incorporated herein by reference in its entirety.

BACKGROUND

Body measurements are used when deciding a size of clothing to purchase. Technologies have been developed to collect body measurements in an accurate and efficient way. For example, three dimensional (3D) body scanners have been used in the apparel industry for decades. However, most 3D body scanners are expensive and not suitable for home use. A number of solutions to develop body measurement methods for clothing shoppers have been proposed in the patent literature. For example, U.S. Patent Application Publication No. 2015/0342266A1 proposes a measurement apparatus made of elastic fabric.

Another approach to measure a body is through a camera. For example, WO Patent Application No. 2012/066555A2 describes a computer program that obtains body measurements through images captured with a camera.

To help reduce the number of users involved in capturing data required for measurement calculation, U.S. Patent Application Publication No. 2017/0024898A1 discloses a method that uses a mirror while taking pictures.

CN Pat. No. 106562503A presents a knitted garment with color lines indicating the location of measurements.

SUMMARY

Embodiments of the present disclosure provide for apparatus, systems, and methods for obtaining body measurements of a user, predicting body measurements of a user, and the like.

One aspect of the present disclosure, among others, includes a coded dimensioning garment, which includes a stretchable fabric that conforms to a wearer's body without substantial compression or distortion of skin of the wearer. The coded dimensioning garment can also include one or more measurement markings of known sizes disposed at one or more known locations on the stretchable fabric. In one aspect, the coded dimensioning garment can be an item of clothing. In another aspect, the coded dimensioning garment can be a stretchable band. In various aspects, the measurement markings can be selected from colored bands, colored lines, areas of color gradients, areas of patterns, areas of motif, or combinations thereof. The coded dimensioning garment can also include non-deformable reference markings secured to the stretchable fabric.

Another aspect of the present disclosure includes a method for predicting body measurements from a user including capturing an image of a user wearing a coded dimensioning garment, wherein the coded dimensioning garment has a plurality of markings of known size and relationship to each other, and wherein the user adopts at least one reference pose near a reference object of known dimensions. At least one image of the user in the reference pose can be uploaded to an application, e.g. a body measurement application. A target image of the reference object is formed in which the real world dimensions of the reference object can be converted to pixel dimensions in the same ratio as the real world dimensions. The user image can be scaled and transformed to match the target image to create a transformed user image. Areas of interest on the user can be made using the markings on the dimensioning garment in the transformed user image. The user's measurements can then be inputted into a prediction model to generate other measurements. In various aspects, the image or images of the user can include a front image and a side image of the user in the reference pose. Data used to generate the prediction model can include anthropometric data, demographic information, weight, body mass index, height, manufacturer data, user preferences, or a combination thereof. Additional user information can be provided by the user, including demographic information, weight, body mass index, height, manufacturer data, or user preferences. In various aspects, the dimensioning garment can be an item of clothing and/or a stretchable band. The known dimensions of the reference object can be provided by the user or can be selected from a set of standard dimensions of predetermined objects. In various aspects, the reference object of known dimensions can be a non-deformable reference marking adhered to the coded dimensioning garment. In various aspects, the user's measurements can be extrapolated manually from photographs or can be extracted using a computer executed program. Additional images can be requested from the user. The user can be provided with at least one error message if a problem is detected with at least one of the images of the user. Problems can include insufficient lighting, distortion of the image, non-detectable garment markings, measurements outside expected values, or combinations thereof.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIG. 1C shows examples of additional postures that may be used to obtain measurements.

FIGS. 10A-10H provide examples of screens rendered through a user interface.

FIGS. 14A-14C provide examples of measurement extrapolation from a user wearing a dimensioning garment.

DETAILED DESCRIPTION

Figure 1A:
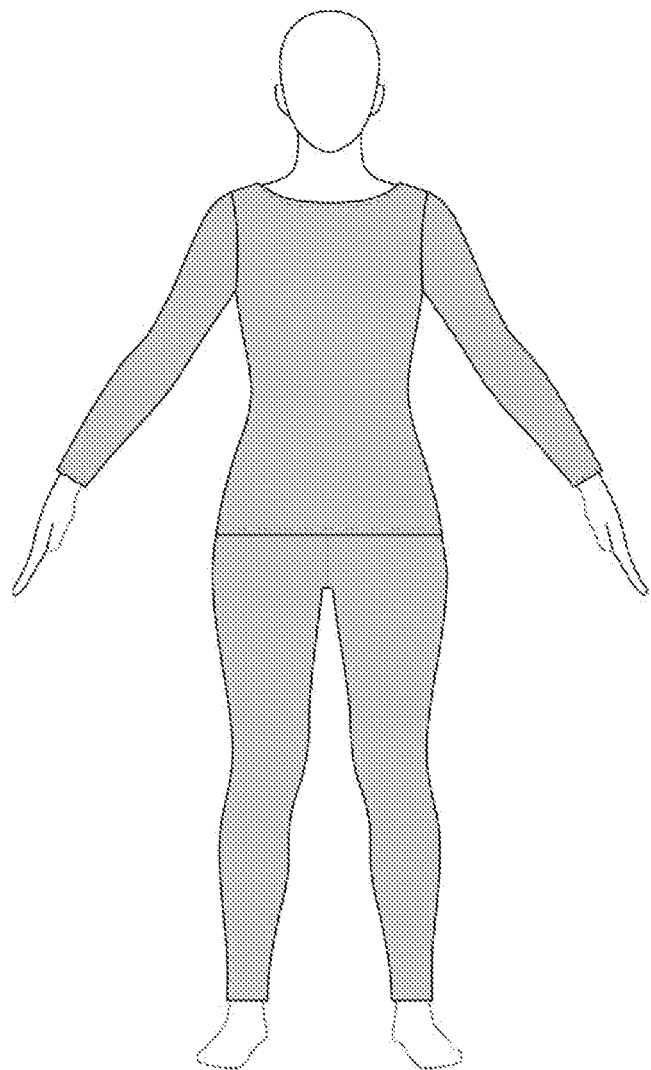
FIG. 1A is a graphical representation of an example of a plain dimensioning garment with full body coverage.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Before the embodiments of the present disclosure are described in detail, it is to be understood that, unless otherwise indicated, the present disclosure is not limited to particular textile materials, manufacturing processes, programming techniques, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The present disclosure illustrates improved apparatus, systems, and methods for measuring body dimensions extracted from one or more two-dimensional (2D) images captured by a user. Measurements of an individual can be taken from captured images or photographs of the individual wearing one or more coded dimensioning garments. Advantages can include achieving accurate measurement results, reduction of user's privacy concerns, and/or integration with other applications. Advantageously, the user does not need specialized facilities or expensive equipment such as 3D scanners to make the measurements. Rather, the user can simply use a digital camera, tablet, smartphone, or similar device to photograph him or herself in a coded dimensioning garment either with or without a reference scale (depending on the design of the garment), which can then be processed to determine the body dimensions.

Embodiments of the present disclosure include a coded dimensioning garment with markings at specific locations that can be aligned with characteristic body features. The coded dimensioning garment (also referred to as a scan apparatus or measurement apparatus) can be a single piece garment or can comprise multiple pieces such as, but not limited to, a unitard, leotard, leggings, bandeau, bra, shorts, shirt, tank top, gloves, hat, socks, knee band, elbow band, head band, or combinations thereof.

Figure 2A:
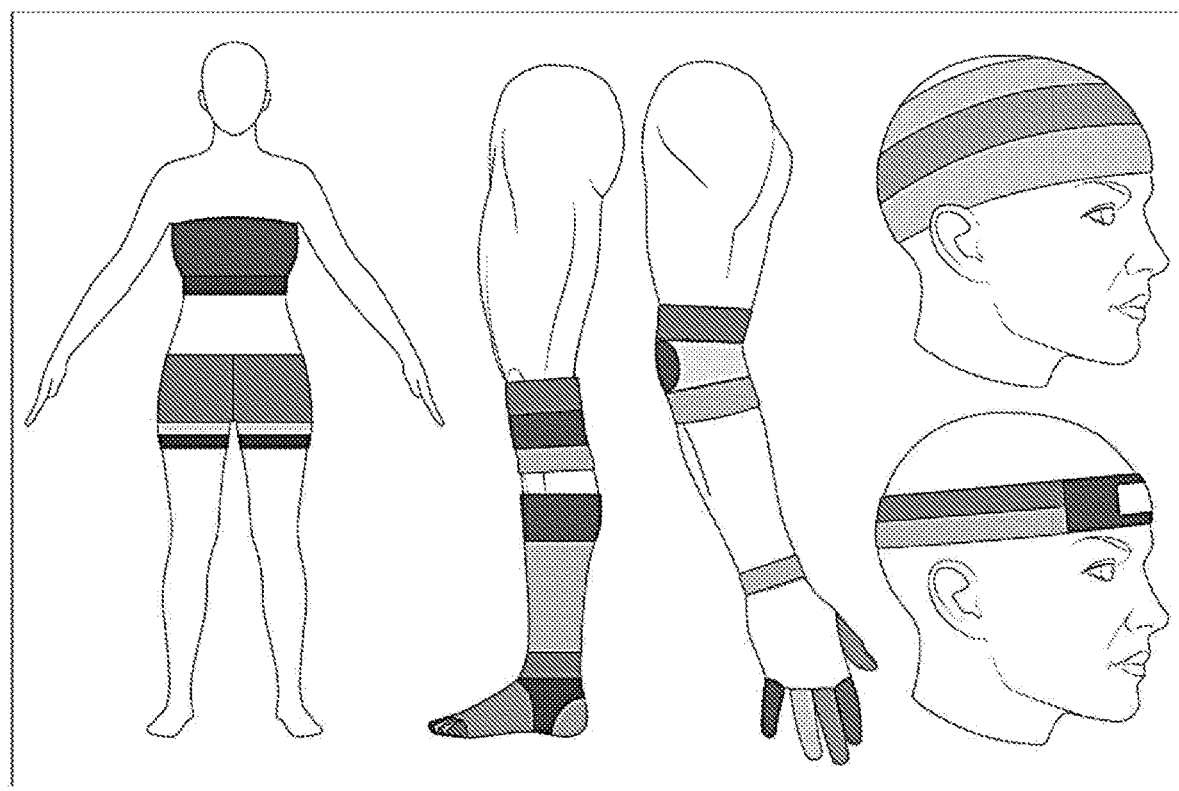
FIG. 2A includes graphical representations illustrating examples of dimensioning garments with partial body coverage.

In various embodiments, the coded areas or garment markings can provide aesthetic attractiveness to customers and users in addition to functionality for measurement purposes. Extracted measurements can be extrapolated based on a reference scale and placements of garment markings. For example, in FIGS. 2A-2B, color bands at bust area and waist area can be used to separate and limit search ranges of the bust width measurement and the waist front width measurement. In some embodiments, markings on the coded dimensioning garment provide an indication of specific measurement locations and aid in the determination of body "edges". In other embodiments, changes in the size and shape of the garment markings can provide information on specific measurements. In various embodiments, patterns or shapes within the garment markings can be used to determine specific measurements. In an embodiment, the garment markings can be used for extracting measurements. The coded markings can be in the form of colored lines or bands at specific locations on the garment designed to coincide with anthropometric measurement locations. This configuration can increase the consistency of user measurements, thereby reducing errors with repeated measurements. In some embodiments, the garment markings can be in the form of regions of color or color gradients. In yet other embodiments, the coded garment markings can be in the form of patterns or motifs. In other embodiments, fiber optics, conductive yarns or ultraviolet inks can be used within the garment to aid in measurement determination. Advantageously, embodiments of the present disclosure eliminate the need for users to input key points, and the entire body can be targeted.

In various embodiments, the dimensioning garment can include one or more non-deformable reference markings such as patches which can serve as a reference scale. In other embodiments, reference objects of known dimensions can be included in the captured images or photographs for scale. In other embodiments, reference measurements such as user height can be used for scale.

In some embodiments, the extracted measurements can be saved and/or compared to repeated measurements that were taken over time. Comparisons of measurements over time can be integrated into fitness tracking or sports training applications to monitor body composition or shape change in addition to weight change. A server can be used to process and store body data of users.

In various embodiments, extracted measurements can be used to select clothing based on a likelihood of fit, or can be used to create customized clothing or accessories. In some embodiments, the extracted measurements can be utilized by an application executed by a processing device or computer, exported to a variety of applications, and/or displayed on a user interface.

Verification tests were conducted on two subjects. The results showed that the difference between the waist circumferences calculated using the disclosed system and extracted through a commercial three-dimensional (3D) body scanner was less than 1.3% (0.39 inch). The calculated waist circumference for subject one was 30.38 inches, while the value measured by the 3D scanner was 30.77 inches. The calculated waist circumference for subject two was 31.92 inches, while the value measured by the 3D scanner was 31.80 inches. The results on hips circumference was less accurate but still less than 2% (0.81 inch). The difference in bust circumference was less than 3% (1.02 inches). These measurements fall within acceptable manufacturing tolerance and ease allowances.

Figure 1B:
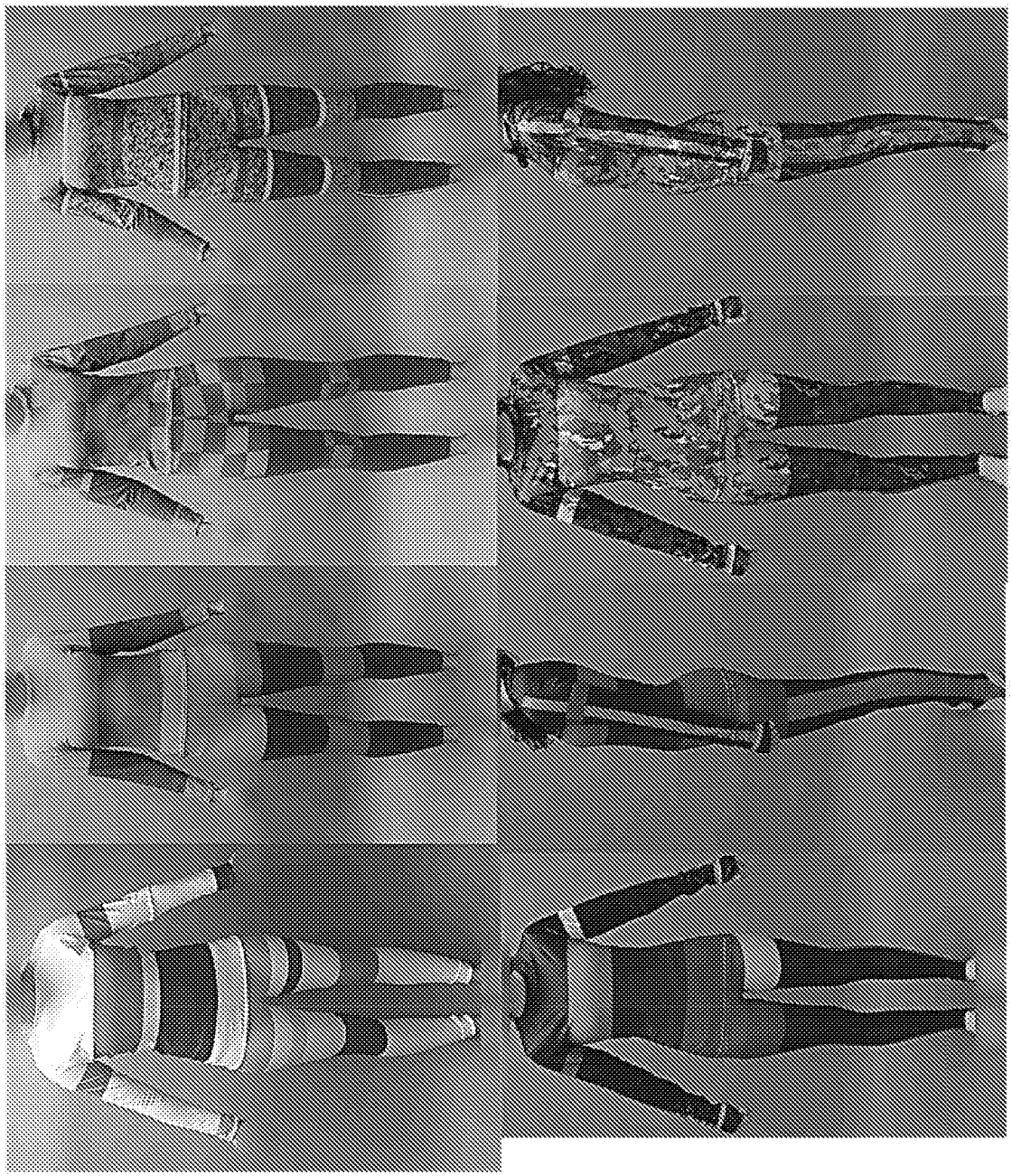
FIG. 1B provides examples of full-body coverage dimensioning garments.
Figure 2B:
FIG. 2B includes graphical representations illustrating examples of alternative clothing styles that can be used as dimensioning garments.

Referring to FIG. 1A, shown is an example of a dimensioning garment. In the example of FIG. 1A, the dimensioning garment includes a close-fitted top and bottom to be worn over most parts of a body of a human subject. Dimensioning garments can be made out of knit, woven, or nonwoven fabric that is thin enough so as not to add or detract from the measurements obtained from the user in any appreciable way (e.g. from about 0.3 mm to about 3.0 mm thick) and stretchable. The fabric can be selected to conform to the shape of the body while minimizing the compression applied to the body by the garment, and without adding bulk that would impact measurement accuracy. At the same time, the coded dimensional garment can decrease users' privacy concerns of having pictures taken while wearing their underwear, which is often the case when measurements are taken using a three dimensional body scanner. FIG. 1B provides examples of alternative full coverage garments, including a gridded version and a camouflage version to add attractiveness to customers while maintaining functionality for measurement purposes. In addition to the garments with full coverage, garments providing partial coverage are also considered. These garments include shorts, sleeveless tops, hats, gloves, bras, socks, and a variety of stretchable bands that can be worn at multiple locations (e.g., knee, elbow, head, etc.), some examples of which are provided in FIG. 2A. As shown, these garments can include multiple bands to identify different regions for measurement. In other embodiments, the color codes can be embedded in existing clothing styles such as, but not limited to, polo shirt, swimwear, and/or close fitted sportswear such as shown in FIG. 2B.

Figure 4:
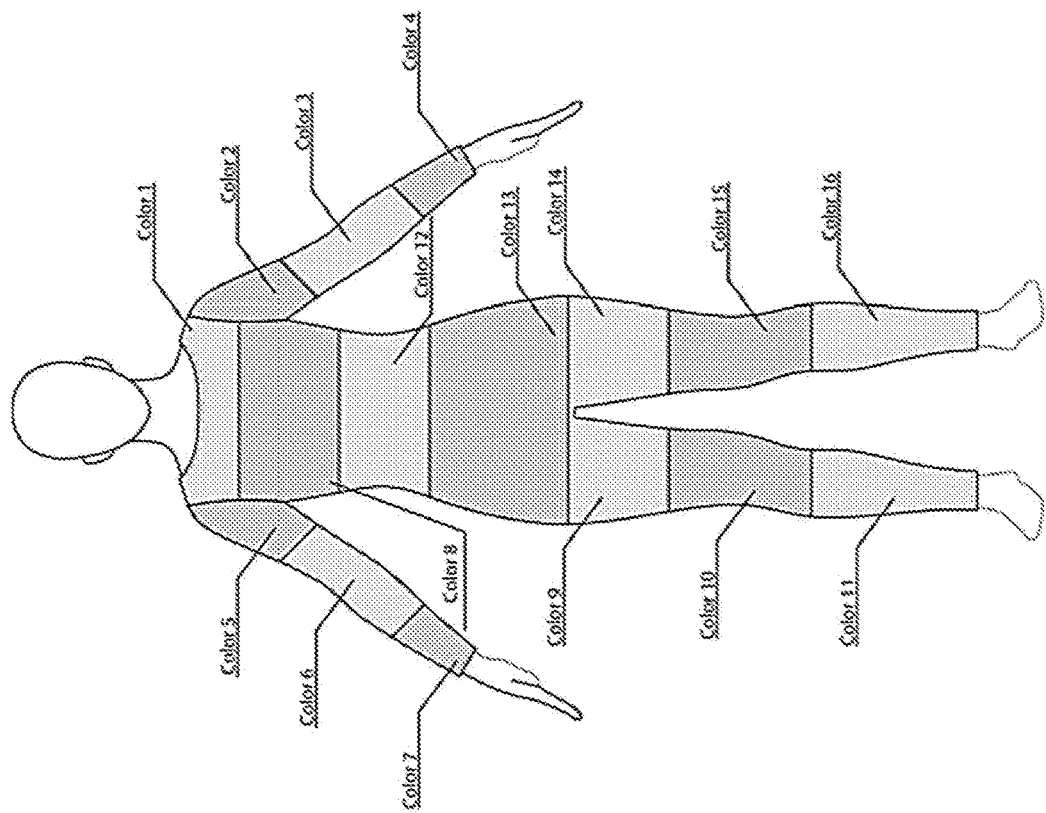
FIG. 4 is a graphical representation of an example of a color coded dimensioning garment with full body coverage.
Figure 3:
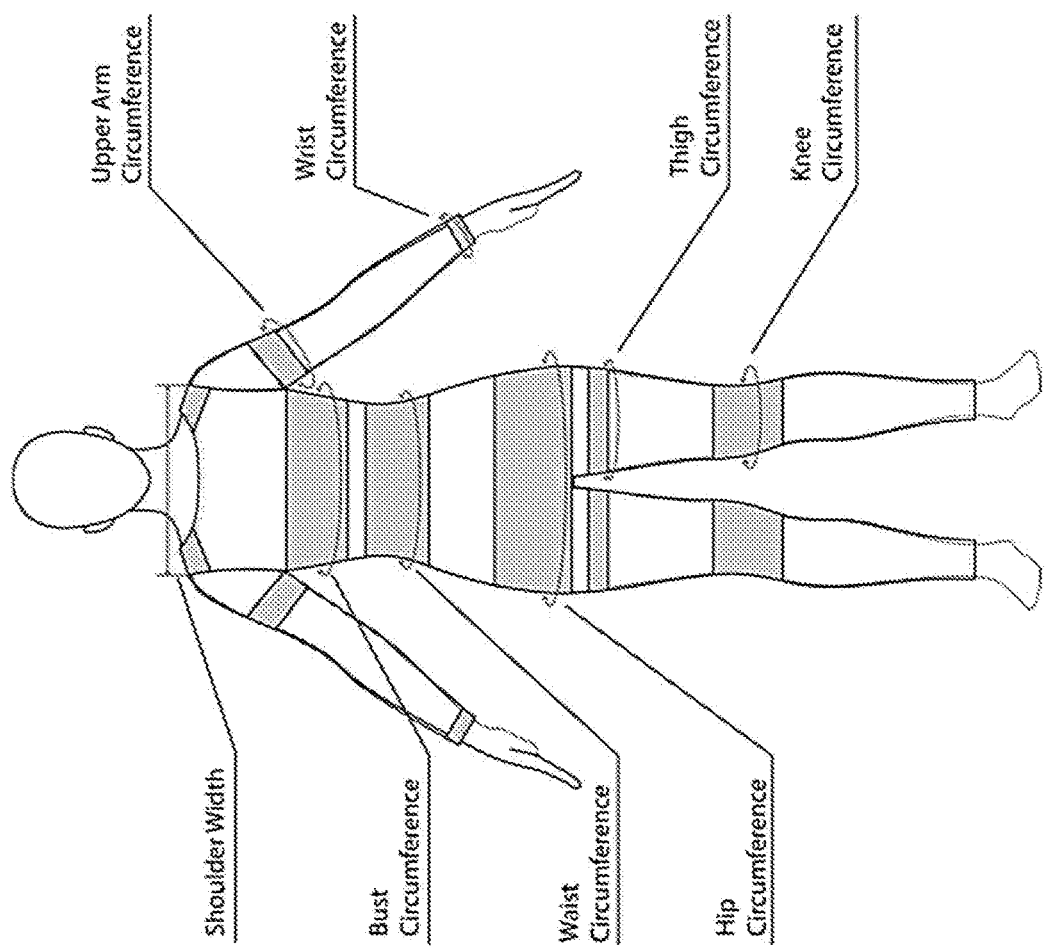
FIG. 3 is a graphical representation of an example of a coded dimensioning garment including measurement code locations in accordance with primary measurements.
Figure 5:
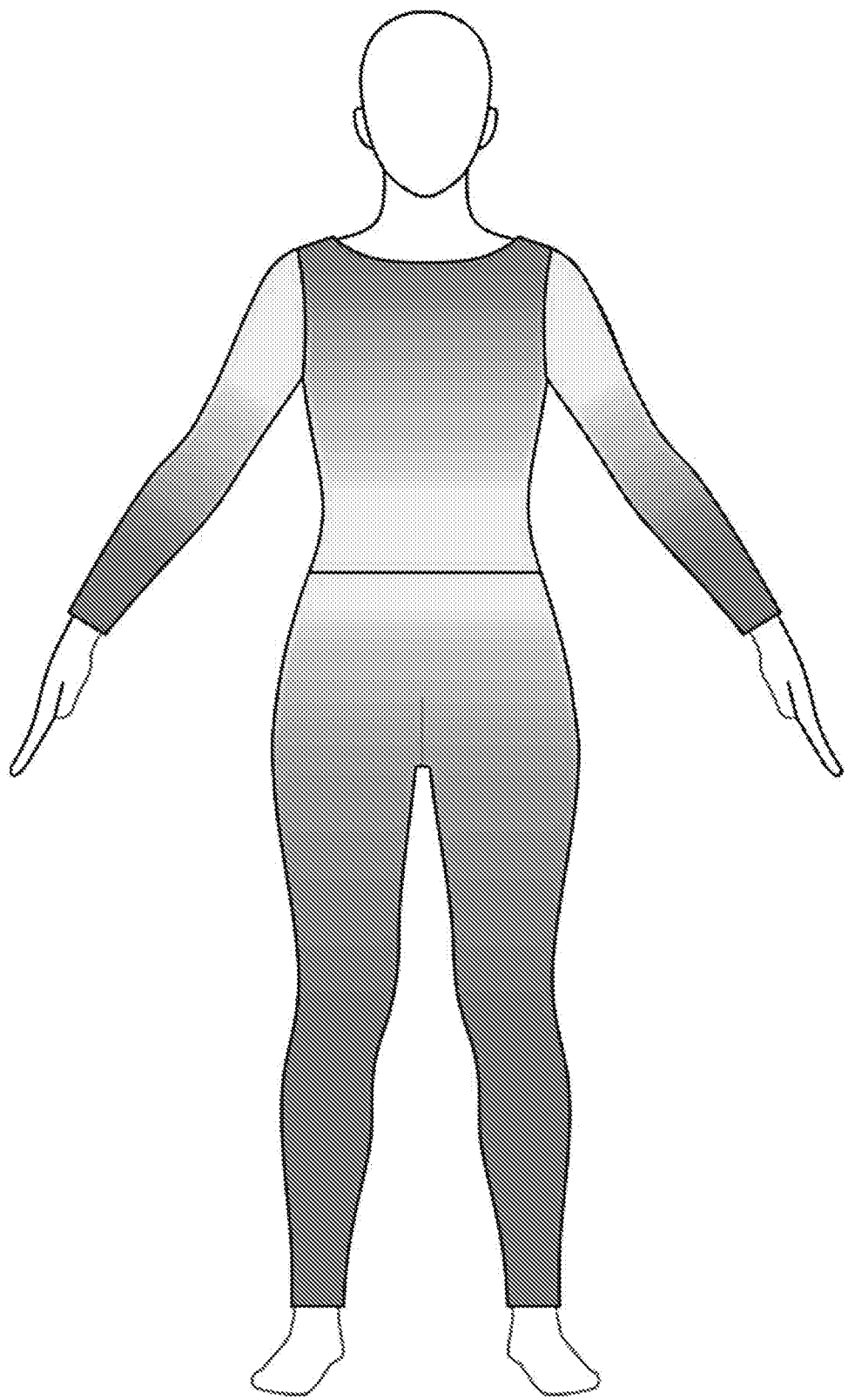
FIG. 5 is a graphical representation of an example of a gradient color coded dimensioning garment with full body coverage.
Figure 6:
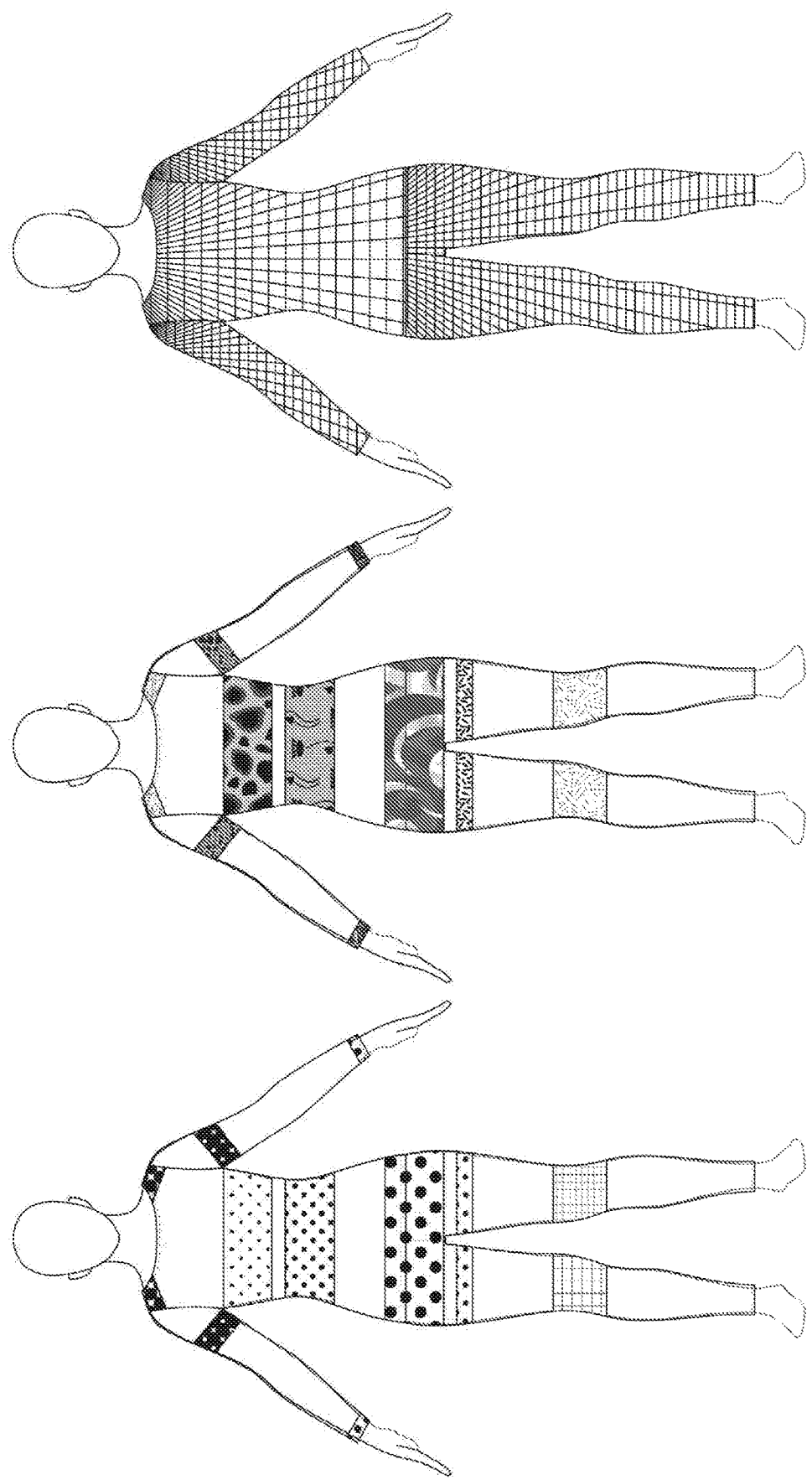
FIG. 6 is a graphical representation of examples of motif/pattern coded dimensioning garments with full body coverage in different scales and resolutions.

The coded dimensioning garment can include measurement codes to improve the measurement extraction process. An example of a coded dimensioning garment and examples of the corresponding body measurement locations is provided in FIG. 3. As shown, body measurements can include, but are not limited to, shoulder width, upper arm circumference, bust circumference, waist circumference, wrist circumference, hip circumference, thigh circumference, knee circumference and/or other dimensions. In this way, desired measurement areas of interest can be indicated to simplify the image analysis process. In some embodiments, the garments are coded with different colors at different locations and in different sizes and shapes. Some examples of coded dimensioning garments are provided in FIGS. 4 and 5. As illustrated in FIG. 4, colors can be varied between adjacent bands. Different color combinations can be used for the torso, each arm and leg. FIG. 5 shows that the colors can be graded between sections or adjacent bands. Alternatively, the color code can be replaced with different motif patterns in different scales, some examples of which are provided in FIGS. 6A-6C. As shown in FIG. 6A, the pattern can be uniform with different scales and resolutions. As in FIG. 6C, the patterns can be different in each of the bands. A variety of motif patters are shown in FIG. 6B. Additionally, the code may be implemented in different fabric structures. For example, the texture of purl stitches is different from rib stitches. When the difference in texture is visible by a camera, it can be used as an indication of locations of measurements. Another feature to consider is the difference in the ability of light transmission. Single jersey knits are usually less see-through than knitted net structures. With the effect of the skin color, the color difference between different knit structures can be used as an indication of area of measuring. When multiple colored yarns are used, colors of final fabrics depend on fabric structures as well. These types of measurement codes are not only functional but also can be aesthetically appealing. The locations, sizes, scales, and shapes of code patterns may vary depending on the requirements of different applications. For example, if the apparatus is designed for the use in size selection, in most cases, only bust circumference, waist circumference, hips circumference, arm length, and inseam length are needed. In these cases, codes on bust, waist, and hips are necessary and using color bands may be sufficient. However, if the apparatus is designed for fitness tracking and coaching, users may want to track the change of some specific muscles. In this case, an apparatus with codes following the map of muscle distribution can be incorporated. The codes can be implemented using printing, knitting, weaving, and sewing. Alternatively, conductive threads can be integrated in the measurement codes to form a circuit that can help better extract body measurements at certain locations. Changes in the sinusoidal shape of the conductive yarns can provide information related to the growth of the body compared to the reference garment when not worn.

Figure 7:
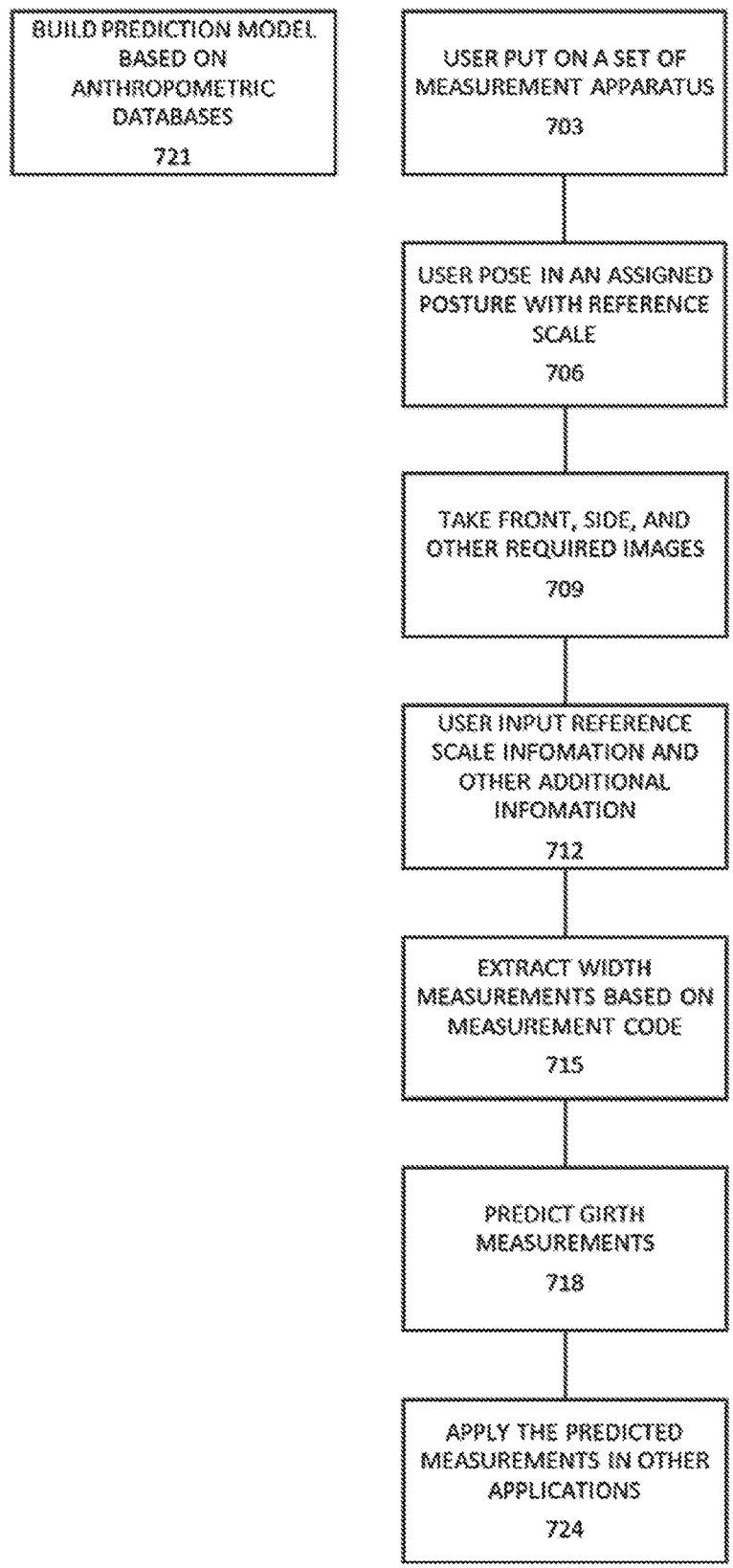
FIG. 7 is a flowchart illustrating an example of a method of the measurement prediction model.
Figure 8:
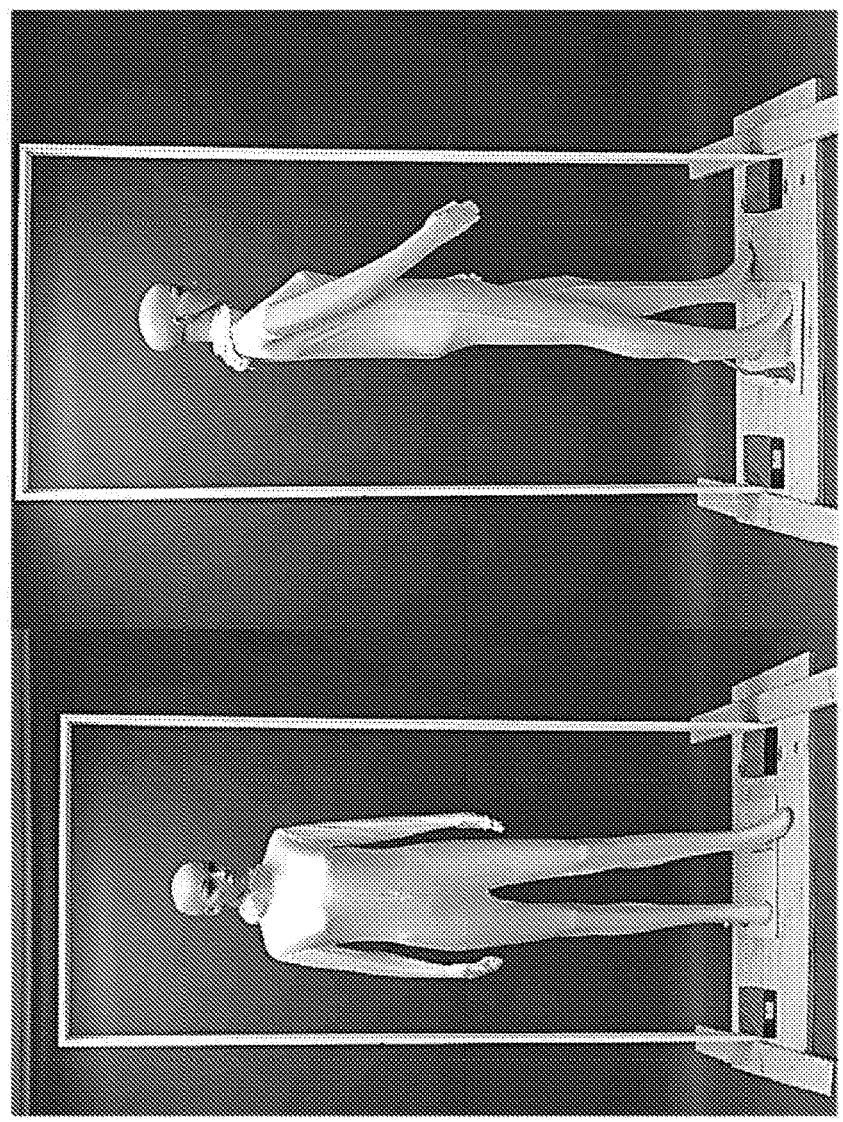
FIG. 8 includes front and side images of an example of a mannequin standing underneath a door frame used as a reference scale.

There is also provided, in accordance with an embodiment of the present disclosure, an example of a method for measuring body features and/or dimensions from images taken by cameras or other image capture devices. The method can be used regularly, such as on a daily basis, to monitor changes in the user's body. A flowchart providing an example of the method is shown in FIG. 7. The procedure of the method begins at 703, where the user is requested to put on the measurement apparatus (e.g., a coded dimensional garment) and organize the garments so that wrinkles are minimized and measurement codes can be located in the intended areas for measurement. The user can then be requested to pose in an assigned posture with a reference scale at 706. For example, the user can be prompted to pick a door frame with known dimensions, however, other objects can also be considered as the reference scale. For instance, patches of known dimensions can be included on the coded dimensional garment and used for scaling. At 709, the user first takes an image of the door frame, then the user is asked to stand underneath the door frame where front and side images of the user standing underneath the door frame are taken with the assistance of another person or tools that can hold the camera. A mannequin is shown as an illustrative example of front and side views under a door frame in FIG. 8. The user can then be asked to input additional information including, but not limited to, dimensions of the door frame or other reference items in the captured images at 712. The captured (e.g., front and side) images are analyzed based on the measurement codes at 715 and a certain number of measurements (e.g., width and length measurements) are extracted. At 718, bodily measurements can be predicted from the extracted measurements. The extracted measurements can be imported into a prediction model built on large anthropometric databases and or databases and collected data information that takes into consideration the measurement apparatus (at 721) to extract other measurements (such as girth measurements). The predicted measurements can then be used for other applications such as size prediction, customized clothing, and fitting estimation at 724.

In the given example, the front and side image pictures were first imported into an open source image editor called ImageJ. In the program, perspective is corrected based on the contour shape of the door frame. With the dimensions of the door frame input by users, the images can be scaled to the size where each pixel represents 0.1 inch or other appropriate scale. In the corrected images, the side bust width can be measured in the coded bust region at the level where a maximum side bust width can be achieved in the side view image. A front bust width can be measured at the same level as the side bust width but in the front view image. The front waist width can be measured in the front view image within the coded waist region at the level of a minimum front waist width. The same level can be used to measure a side waist width in the side view image. The level of the hips width can be determined by both the front view and side view images. They can be measured at the level where the sum of the front hips width and the side hips width is the largest within the coded hips areas. All width measurements are measured paralleled to the floor. When capturing a width measurement at a certain height level, a horizontal straight line is drawn from the edge of the coded measurement region on one side to the other side. The length of the line can then be measured in pixels and then converted into inches or meters.

Additional images may be needed to help the image clean-up process. This step can be omitted if the measurements can be extracted from the initially submitted images. In some embodiments, additional images may be requested from the user. For example, the user can be provided with an error message if additional measurements are needed. This may be needed because the image contains problems such as, e.g. insufficient lighting, distortion of the image, non-detectable garment markings, measurements returned outside expected values or other problems.

Figure 9:
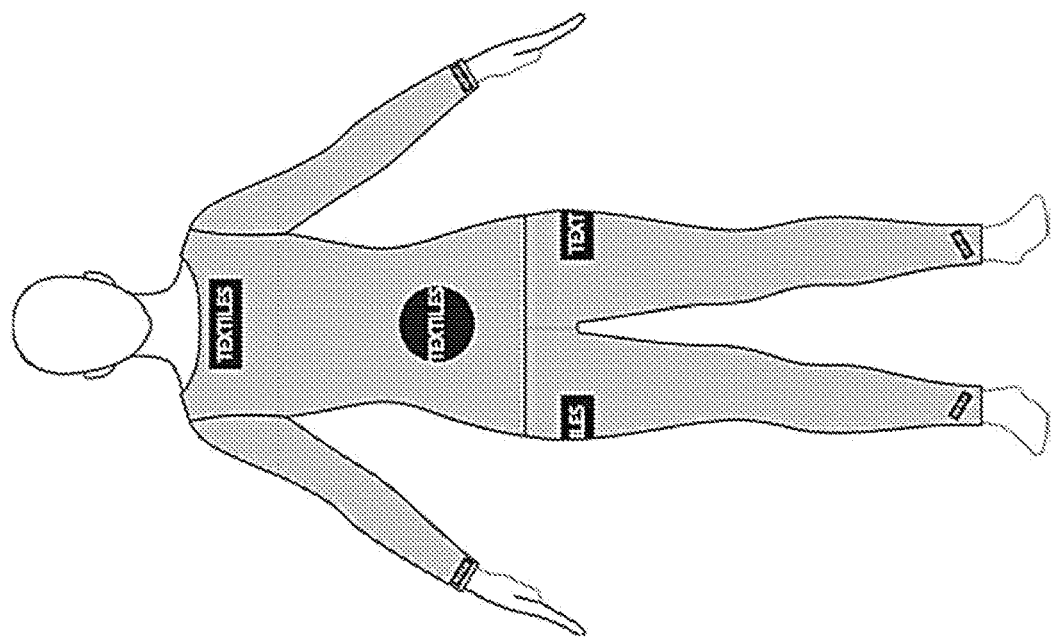
FIG. 9 is a graphical representation of an example of a coded dimensioning garment including non-stretch patches as a reference scale.

Regarding choosing the reference scale, in some embodiments, the door frame can be replaced with the height of the user. In other implementations, one or more non-deformable (non-stretchable) patches with known dimensions can be used. A graphical representation of an example of non-deformable patches is provided in FIG. 9. As shown, a plurality of reference patches can be secured at different locations on the coded dimensional garment(s). The patches can also be designed with a brand logo. The non-deformable material of the patch can be woven fabric, leather, and even metal. The design can be embroidered, jacquard woven, engraved, laser cut, embossed, and the like. Detailed instructions can be given to the user to help him/her position himself/herself in a correct position and posture. To help correct the situation when the user is slightly forward of or behind the doorframe, more than one reference scale can be used. For example, the door frame can be combined with the height of the user. Another approach is to slightly adjust the scale based on the foot location of the user in relation to the bottom line of the door frame. If the user is slightly forward then the image can be scaled based on the distance between the user's feet and the line, and vice versa. The door frame can help adjust distortion due to perspective effects which happen when a camera is not positioned at the center front of the user. In other embodiments, the reference scale can be calculated using other applications, such as augmented reality platforms associated with a user's device.

Regarding the information input by the user, besides the dimension information for the reference scale, in some embodiments, users can be asked to type in their demographic data such as their age, sex, ethnicity, etc. This can help filter prediction parameters in the subsequent steps. In other embodiments, users may need to input additional information such as their weight, fitting preference, and previous shopping experience. In some scenarios, information from the camera may be needed, such as model, lens type, or shooting mode. An example of the user interface is shown in FIGS. 10A-10H. FIG. 10A is an example of an initial user interface screen. The user can input account login information into fields (FIGS. 10B and 10C). The user can input additional information as discussed above, e.g. age, weight, height. User instructions, help videos, and other information can be provided to the user (FIG. 10E). FIG. 10F is an example of a screen for the user to provide images e.g. front and side images while wearing the dimensioning garments. The user can upload measurements of a reference object, such as a doorframe into the user interface, as shown in FIG. 10G. FIG. 10H shows an example of a results screen on which measurements extracted from the dimensioning garment(s) can be displayed.

Regarding image capture, in some embodiments, a computerized application can accommodate the need to control the camera or other image capture device to take pictures, analyze the image data, and collect the user input. The body measurement application can be used on a mobile device such as, e.g., smartphone, digital camera, tablet, laptop, and the like. Images can also be taken on one image capture device and provided to an application on a second device. For example, by having a door frame template on a device screen when the images are taken, it helps users find the right angle and location to take the images. Once the camera information is obtained by the body measurement application, the information can be used to guide the image capture. In some embodiments, images can be taken at other angles not limited to front and side images. In other embodiments, a web server can be created for user to upload their images and have their measurements extracted. If user measurements of the reference object are not provided, the reference object can be measured manually in a program such as ImageJ or Adobe Illustrator, or automated via algorithms in the computerized application. The process can be automated using image processing APIs, such as open source platforms (e.g. OpenCV and/or SciKit-Image).

Figures 11A, 11B:
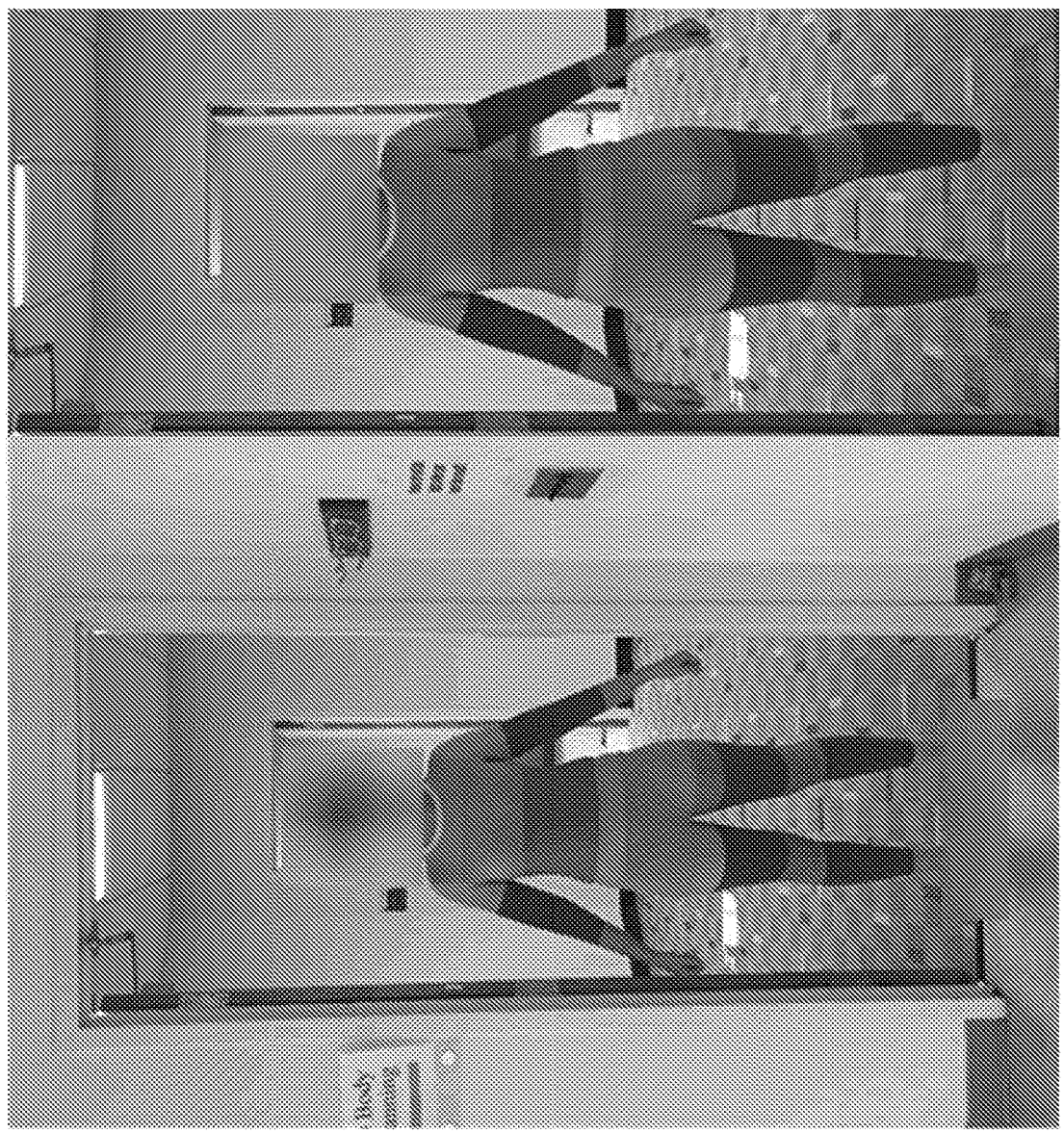
FIGS. 11A-11E graphically illustrate examples of steps used in image processing.
Figures 11C, 11D, 11E:
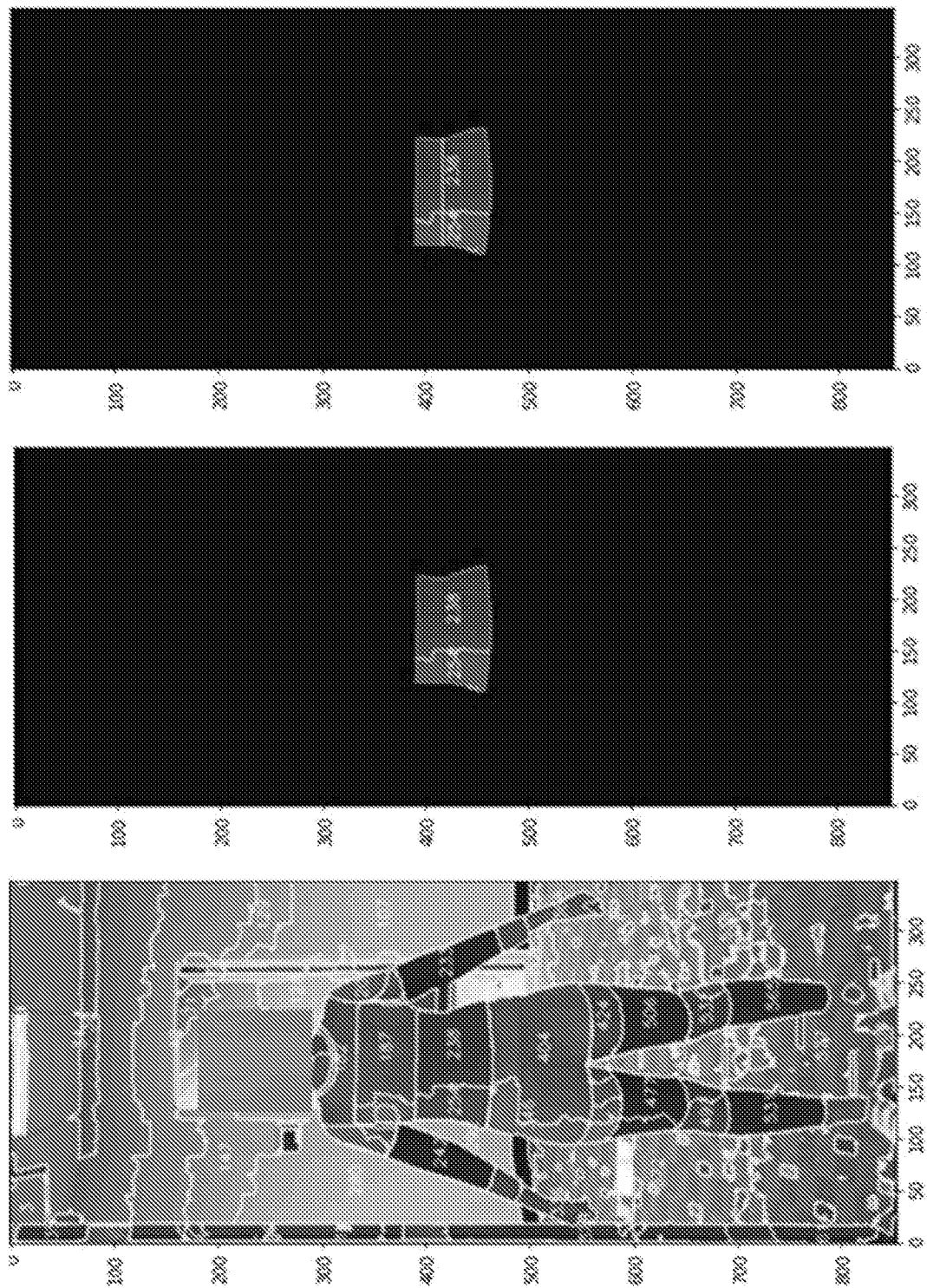

The program can be saved in the server to allow timely updating. An example of how the images can be analyzed is illustrated in FIGS. 11A-E: (1) an image is first provided (FIG. 11A); (2) a reference object used to determine scale (in this example, a door frame) is detected and the image is cropped so that only the area within the door frame is kept (FIG. 11B); (3) perspective distortion within the cropped area is corrected; (4) the image is over-segmented (FIG. 11C); (5) regions of specific interest are selected (in this example, the waist area is selected)(FIG. 11D); (6) a measurement is extracted at the defined location (FIG. 11E). The same process applies to the side image. In the example illustrated in FIGS. 11A-E, the reference object is a doorframe. In other embodiments, the reference object can be a non-deformable patch of known dimensions on a dimensioning garment worn by the user. The user image can be scaled and deformed based on the known dimensions of the non-deformable patch in place of step 2 above. In other embodiments, the reference scale can be calculated using developed augmented reality APIs, (e.g. ARKit by Apple Inc.) in which case no reference objects are needed from the users. Steps 3-6 could follow as described above.

Figure 12:
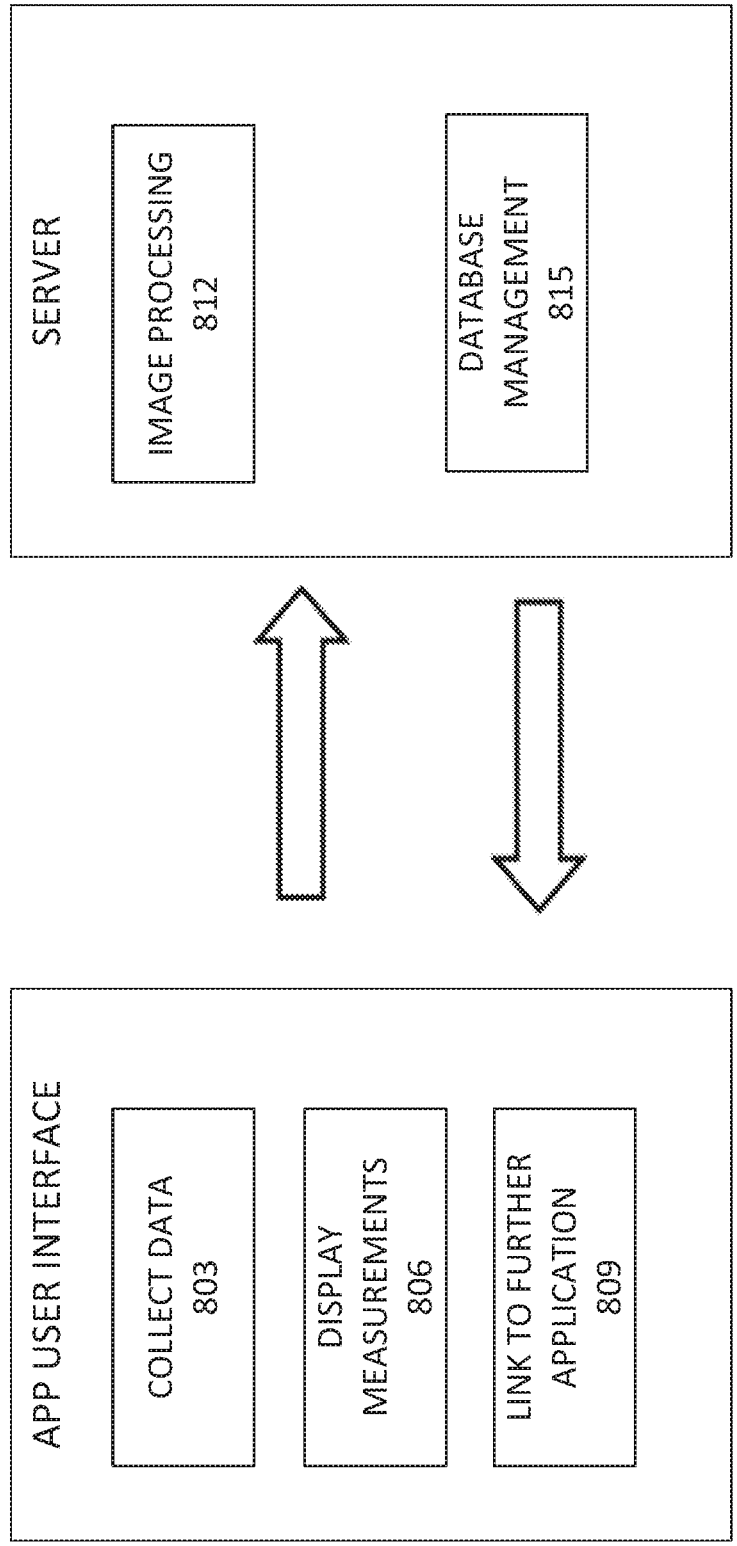
FIG. 12 is an example of a developed app implemented on a user device and used in conjunction with the dimensioning garments.

An example of how data can be communicated between different parts of the system is illustrated in FIG. 12. Image data and other required information can be input through a user interface on a device such as a smartphone or other image capture/input device. Next, the images can be pre-processed on the device. The processed images and the collected user data 803 can be uploaded to a server where images can be further analyzed at 812. The measurement prediction models can be saved on the server and used for additional measurement calculations. The calculated measurements can be kept on the server to allow the user to access the information in the future or linked to a further application at 809. When called by the user, the measurement data can be sent to the device and displayed in the app at 806 or linked to a further application at 809. The information obtained from the user interface can be stored in one or more data stores. Database management 815 of the data stores can be provided using available web services.

Regarding the user's standing postures, a default pose is illustrated in FIG. 1A. Additional poses, such as the examples provided in FIG. 1C may be added depending on the locations of the target measurements to obtain measurements that may be obscured in the default poses or to cross-reference measurements. The default poses maximize the visibility of the coded regions of interest and minimize the distortion of these regions.

There is also provided, in accordance with various embodiments of the present disclosure, a method of building prediction models for measurement calculation with the extracted measurements from images taken using a camera. The prediction models can be built on anthropometric databases. Statistical and data mining methods can be applied to generate formulae to predict body measurements based on measurements from user images. For example, upper arm circumference can be predicted for a user based on linear measurements taken from the images and known values from the anthropometric databases. Demographic information, height, weight, body mass index (BMI), and other useful data can be used as filters to increase the accuracy of the prediction. Regarding statistical models used in the analysis, in some embodiments, regression can be used.

For instance, a multi-linear regression model was used to generate the prediction model measurements. Demographic information can be used to filter pre-existing and future anthropometric databases to increase the accuracy of the calculated prediction models. People from different demographic backgrounds may vary in their body shapes. For example, males and females have different body shapes. When predicting their body measurements using width measurements extracted from images, different parameters are needed for men and women. Age can also be a factor in body shape. For example, a female teenager's body shape tends to be different from missy or mature body shapes.

It may be beneficial to divide a group into sub-groups based on a certain feature or not. Therefore, generating multiple prediction models with parameters based upon different sections of a body measurement database can decrease the error range of prediction. The determination of how to use the demographic data to filter the population can be determined and managed based on literature reviews and pattern making experience. However, machine learning algorithms can be included to automate the process. In other words, it is possible to let machine learning algorithms decide whether it is necessary to subdivide groups. Examples of anthropometric databases currently include the SizeUSA data and the Civilian American and European Surface Anthropometry Resource (CAESAR) data. However, all of these existing database body measurement data were measured on subjects wearing underwear, while width measurements from the images are measured over the coded dimensioning garment. To improve the prediction models, additional body data can be collected from subjects while wearing underwear and again while wearing the coded dimensioning garment to create improved linkages between measurements taken in underwear and measurements taken in the coded dimensioning garment.

Figures 13A, 13B, 13C:
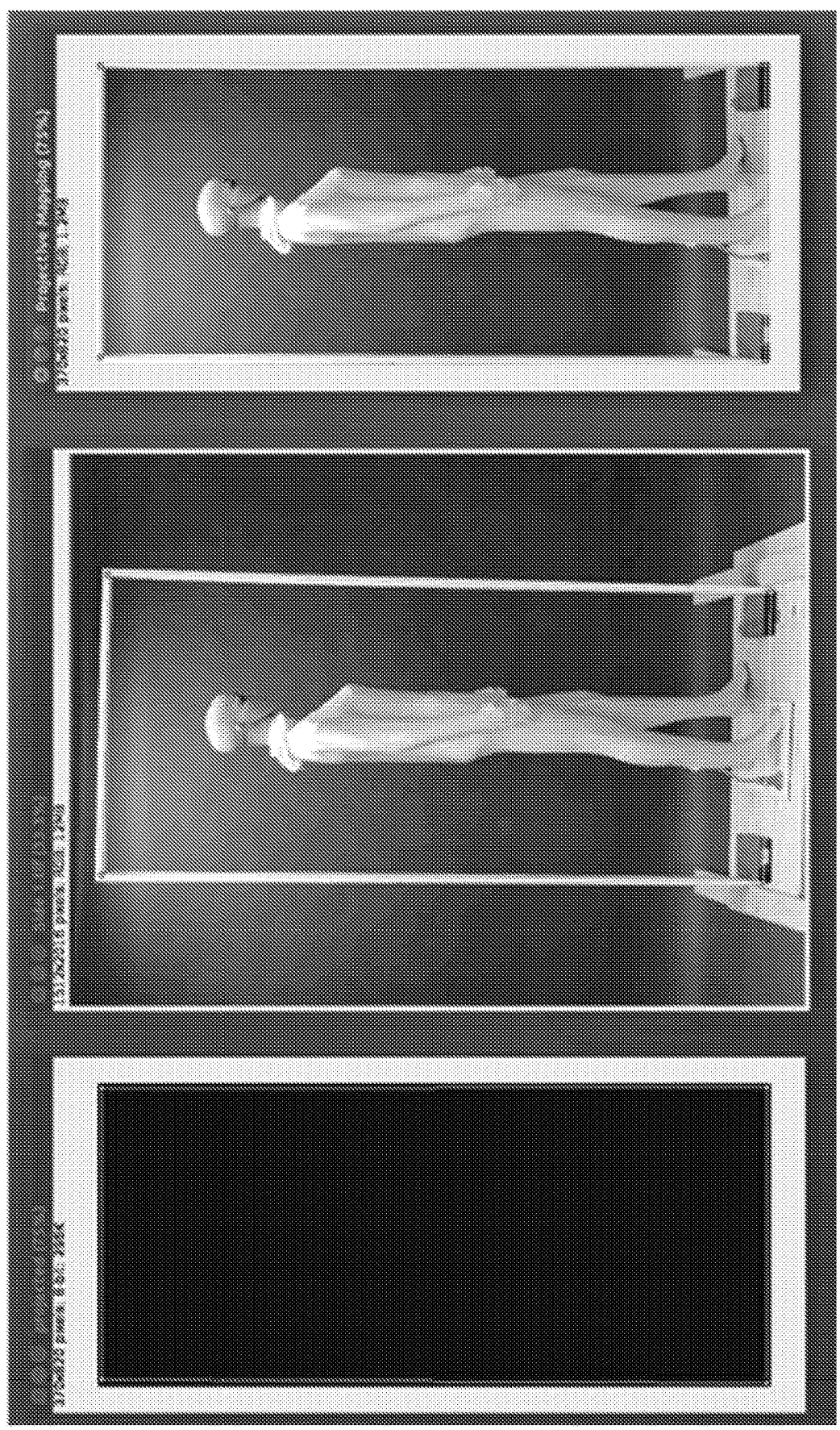
FIGS. 13A-13C show an example of a target image and reference image alignment for scaling purposes.

To build the prediction models, the user-submitted images can be imported by the application. A target image can be created based on the dimensions of the reference object. For example, if the reference object in the reference image is a door frame having the dimensions 35"×85" then the target image can have the same ratio of dimensions in pixels, i.e. width=370 pixels and height=870 pixels, including 10 pixels as the margin. The user image can then be scaled and aligned to the target image to match the dimensions and correct for any rotation. To illustrate this, an example of a door frame target image is shown in FIG. 13A. A user image containing a door frame reference object is shown in FIG. 13B, and the resulting transformed user image is shown in FIG. 13C. An algorithm, such as open source affine mapping algorithms, can be applied to further tune the transformation to allow for accurate measurement. The body measurements of interest can be measured using a line across the area of interest based upon the markings on the coded dimensioning garment in at least one view (e.g. a user image taken in front view). FIGS. 14A and 14B provide an example of images of a user wearing a coded dimensioning garment and FIG. 14C shows linear measurements of the area of interest highlighted. For example, in FIGS. 14A and 14B, a measurement is being taken across the hips, which corresponds the measurements at line 5 and 6 of the results screen in FIG. 14C. The circumference of the body area of interest can then be predicted using a combination of statistical methods such as multiple linear regressions derived from predictions based on anthropometric databases. Example calculations taken from the image measurements can be expressed as:

$$BustCircumference = A + B*FrontWidthBust + C*SideWidthBust \quad (1)$$

$$WaistCircumference = D + E*FrontWidthWaist + F*SideWidthWaist \quad (2)$$

$$HipsCircumference = G + H*FrontWidthHips + J*SideWidthHips \quad (3)$$

where the "FrontWidth" and "SideWidth" variables represent measurements taken from the user images, and the letter variables are values which can be generated using linear regression analysis or other appropriate regression analysis techniques. The values can then be entered into an appropriate regression equation developed based on the anthropometric data for the user's demographics. In equations 1-3, above, the variables A, D, and G are constants, and variables B and C, E and F, and H and J are regression coefficients for their respective independent variables. For example, to calculate bust circumference of the user, linear values of the pixels are measured across the bust in the front view (FrontWidthBust) and the side view (SideWidthBust), and then entered into Equation (1) derived from anthropometric data appropriate for the user's demographics.

Measurements and prediction models can be generated manually or using an automated system for use in many applications. The predicted measurements can include but are not limited to predictions of the circumference of body areas from the linear measurements, interpolation of non-measured areas from measurements of known areas, and/or shape or fit prediction models. In one implementation, an evaluation of 36 subjects determined values of A=1.6175, B=1.3955, C=1.9894, D=−0.29566, E=1.87049, F=1.28460, G=2.62081, H=1.92351, and J=0.91862. These prediction models produced good results.

Figure 15:
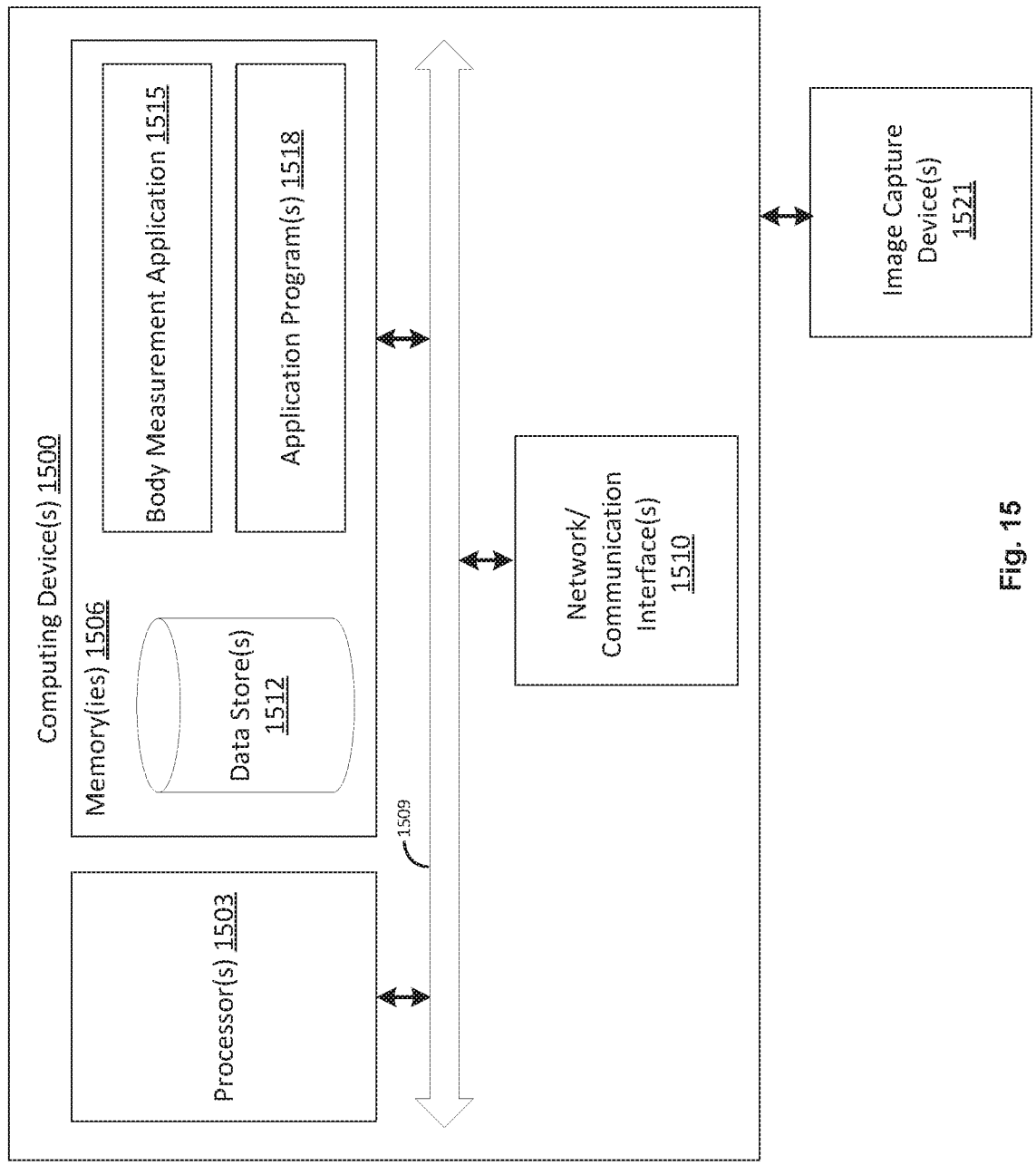
FIG. 15 is an example of a computing device that can be used with the body measurement application of FIG. 12, in accordance with various embodiments of the present disclosure.

With reference to FIG. 15, shown is a schematic block diagram of a computing device 500. In some embodiments, among others, the computing device 1500 may represent a mobile device (e.g., a smartphone, tablet, computer, etc.). Each computing device 1500 includes at least one processor circuit, for example, having a processor 1503 and a memory 1506, both of which are coupled to a local interface 1509. To this end, each computing device 1500 may comprise, for example, at least one server computer or like device, which can be utilized in a cloud based environment. The local interface 1509 may comprise, for example, a data bus with an accompanying address/control bus or other bus structure as can be appreciated.

In some embodiments, the computing device 1500 can include one or more network/communication interfaces 1510. The network/communication interfaces 1510 may comprise, for example, a wireless transmitter, a wireless transceiver, and/or a wireless receiver. As discussed above, the network interface 1510 can communicate to a remote computing device using a Bluetooth, WiFi, or other appropriate wireless protocol. As one skilled in the art can appreciate, other wireless protocols may be used in the various embodiments of the present disclosure. In addition, the computing device 1500 can be in communication with one or more image capture device(s) 1521. In some implementations, an image capture device 521 can be incorporated in the computing device 1500 and can interface through the local interface 1509.

Stored in the memory 1506 are both data and several components that are executable by the processor 1503. In particular, stored in the memory 1506 and executable by the processor 1503 can be a body measurement program 1515 and potentially other application program(s) 1518. Also stored in the memory 1506 may be a data store 1512 and other data. In addition, an operating system may be stored in the memory 1506 and executable by the processor 1503.

It is understood that there may be other applications that are stored in the memory 1506 and are executable by the processor 1503 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 1506 and are executable by the processor 1503. In this respect, the term "executable" means a program file that is in a form that can ultimately be run by the processor 1503. Examples of executable programs may be, for example, a compiled program that can be translated into machine code in a format that can be loaded into a random access portion of the memory 1506 and run by the processor 1503, source code that may be expressed in proper format such as object code that is capable of being loaded into a random access portion of the memory 1506 and executed by the processor 1503, or source code that may be interpreted by another executable program to generate instructions in a random access portion of the memory 1506 to be executed by the processor 1503, etc. An executable program may be stored in any portion or component of the memory 1506 including, for example, random access memory (RAM), read-only memory (ROM), hard drive, solid-state drive, USB flash drive, memory card, optical disc such as compact disc (CD) or digital versatile disc (DVD), floppy disk, magnetic tape, holographic storage, or other memory components.

The memory 1506 is defined herein as including both volatile and nonvolatile memory and data storage components. Volatile components are those that do not retain data values upon loss of power. Nonvolatile components are those that retain data upon a loss of power. Thus, the memory 1506 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1503 may represent multiple processors 1503 and/or multiple processor cores, and the memory 1506 may represent multiple memories 1506 that operate in parallel processing circuits, respectively. In such a case, the local interface 1509 may be an appropriate network that facilitates communication between any two of the multiple processors 1503, between any processor 1503 and any of the memories 1506, or between any two of the memories 1506, etc. The local interface 1509 may comprise additional systems designed to coordinate this communication, including, for example, performing load balancing. The processor 1503 may be of electrical or of some other available construction.

Although the body measurement program 1515 and other application program(s) 1518 described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the body measurement application 1515 and the application program 1518, that comprises software or code can be embodied in any non-transitory computer-readable medium for use by or in connection with an instruction execution system such as, for example, a processor 1503 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the body measurement application 1515 and the other application program(s) 1518, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 1500, or in multiple computing devices in a same computing environment. To this end, each computing device 1500 may comprise, for example, at least one server computer or like device, which can be utilized in a cloud based environment. Additionally, it is understood that terms such as "application," "service," "system," "engine," "module," and so on may be interchangeable and are not intended to be limiting.

Applications of this disclosure include but are not limited to body measurement extraction, size prediction, customization, fitness tracking, exercise coaching, and sports related applications such as muscle development monitoring.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method for predicting body measurements from a user comprising:
    capturing an image of a user wearing a coded dimensioning garment, wherein the coded dimensioning garment has one or more markings of known size and relationship to each other, and wherein the user is in at least one reference pose near a reference object of known dimensions in the image;
    uploading at least one image of the user in the reference pose to an application;
    forming a target image of the reference object in which the real world dimensions of the reference object are converted to pixel dimensions in the same ratio as the real world dimensions;
    scaling and transforming the image of the user to match the target image to create a transformed user image;
    measuring areas of interest on the user using the one or more markings on the dimensioning garment in the transformed user image to generate user's measurements; and
    providing the user's measurements into a prediction model to generate predicted measurements.

2. The method of claim 1, wherein the at least one image of the user includes a front photograph and a side photograph of the user in the reference pose.

3. The method of claim 1, wherein data used to generate the prediction model includes anthropometric data, demographic information, weight, body mass index, height, manufacturer data, user preferences, or a combination thereof.

4. The method of claim 3, further comprising obtaining additional user information provided by the user, the additional user information comprising demographic information, weight, body mass index, height, manufacturer data, user preferences, or a combination thereof.

5. The method of claim 1, wherein the at least one dimensioning garment is an item of clothing.

6. The method of claim 1, wherein the at least one dimensioning garment is a stretchable band.

7. The method of claim 1, wherein the known dimensions of the reference object are provided by the user or are selected from a set of standard dimensions of predetermined objects.

8. The method of claim 1, wherein the user's measurements are extrapolated manually from photographs.

9. The method of claim 1, wherein the user's measurements are extracted using a computer executed program.

10. The method of claim 1, further comprising requesting additional images from the user.

11. The method of claim 1, further comprising providing the user with at least one error message if a problem is detected with at least one of the images of the user.

12. The method of claim 11, wherein the problem is selected from insufficient lighting, distortion of the image, non-detectable garment markings, measurements outside expected values, or a combination thereof.

13. The method of claim 1, wherein the reference object of known dimensions is a non-deformable reference marking adhered to the coded dimensioning garment.

\* \* \* \* \*